United States Patent
Matson et al.

(10) Patent No.: US 6,268,141 B1
(45) Date of Patent: Jul. 31, 2001

(54) IMMOBILIZATION OF UNMODIFIED BIOPOLYMERS TO ACYL FLUORIDE ACTIVATED SUBSTRATES

(75) Inventors: Robert S. Matson, Orange; Raymond C. Milton, La Habra, both of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/312,095

(22) Filed: May 12, 1999

(51) Int. Cl.$^7$ .......................... C12Q 1/68; G01N 33/543; B01L 9/00; A61K 38/00
(52) U.S. Cl. ....................... 435/6; 435/7.1; 435/7.5; 435/180; 435/181; 436/501; 436/518; 422/50; 422/68.1; 422/104; 530/333; 530/334; 530/402; 530/810; 530/811; 530/815
(58) Field of Search ................... 435/6, 7.1, 7.5, 435/176, 180, 181, 810; 422/50, 68.1, 101, 104; 530/333, 334, 402, 811, 815, 810; 536/25.3; 436/63, 89, 94, 518, 501, 172

(56) References Cited

U.S. PATENT DOCUMENTS

| | | | |
|---|---|---|---|
| 5,011,861 | * | 4/1991 | Coull et al. ............... 521/53 |
| 5,554,501 | * | 9/1996 | Coassin et al. ............ 435/6 |
| 5,602,207 | * | 2/1997 | Boyd et al. ............ 525/326.2 |
| 5,717,075 | * | 2/1998 | Boyd et al. ............. 530/402 |
| 5,985,567 | * | 11/1999 | Rampal .................. 435/6 |
| 6,037,124 | * | 3/2000 | Matson .................. 530/402 |

FOREIGN PATENT DOCUMENTS

WO 97/46597  12/1997  (WO).

OTHER PUBLICATIONS

Hagaman, Edward W., et al; "Synthesis and Solid State $^{13}$C and $^{19}$F NMR Characterization of Aliphatic and Aromatic Carboxylic Acid Fluoride Polymers", *Anal Chem.* 1997, 69, 3950–3958.

* cited by examiner

*Primary Examiner*—Long V. Le
*Assistant Examiner*—Gailene R. Gabel
(74) *Attorney, Agent, or Firm*—William H. May; Arnold Grant (57) ABSTRACT

A method of attaching unmodified biopolymers, particularly, unmodified polynucleotides, directly to a solid support is provided. The method includes the steps of (a) providing unmodified biopolymers; (b) providing a solid support having at least one surface comprising pendant acyl fluoride functionalities, and (c) contacting the unmodified biopolymers with the solid support under a condition sufficient for allowing the attachment of the biopolymers to the solid support. The unmodified biopolymers may be nucleic acids, polypeptides, proteins, carbohydrates, lipids and analogues thereof. The unmodified polynucleotides may be DNA, RNA or synthesized oligonucleotides. The DNA may be single or double stranded. A device including a solid support and unmodified biopolymers attached to the solid support by reaction with the pendant acyl fluoride functionalities of the solid support is also provided. The methods and devices of the present invention may be used in performing hybridization assays and immunoassays.

27 Claims, 7 Drawing Sheets

PRIMER ARRAY CREATED BY BIODOT DISPENSER

Fig. 1a

actin    G3PDH    p53    TNF actin cDNA
microglobulin cDNA
G3PDH cDNA
p53 cDNA
transferrin cDNA
TNF cDNA cDNA ARRAY CREATED BY BIODOT DISPENSER

MEAN ± SD/ PROBE UN VS AMINO

Fig. 5

SIGNAL INTENSITIES AS
A PERCENTAGE OF BAPA

IMMOBILIZED PROTEIN AT 0.5 mg/mL, FOLLOWED
BY Rb ANTI-Gt IgG AT 1:100 DILUTION IN TBS

*Fig. 8*

IMMOBILIZING Ab ON BIOTIPS
Gt ANTI-BIOTIN ON TIPS                    MARCH 26, 1998

1.0 mg/mL Ab
IN PBS 1.              2.

0.5 mg/mL Ab
IN CARBONATE, pH 10

3.              4.

INCUBATION TIME:           30 MIN.         60 MIN.
SOURCE FILE: 80326B.FTS                 (GOATAB.BMP)

*Fig. 10*

STREPTAVIDIN
IMMOBILIZED
IN pH 9
CARBONATE
BUFFER

5X DENHARDT'S SOLN.
(CONTROL)

CASEIN IN CARBONATE
BUFFER. pH 8.5

S&S BLOCKING POWDER IN
CARBONATE BUFFER. pH 8.5

5X DENHARDT'S SOLN.
PREMOISTENED
WITH EtOH

CASEIN IN TBS
pH 7.5

S&S BLOCKING POWDER IN
TBS. pH 7.5

*Fig. 9*

IMMOBILIZATION OF UNMODIFIED BIOPOLYMERS TO ACYL FLUORIDE ACTIVATED SUBSTRATES

BACKGROUND OF THE INVENTION

1. Area of the Art

The invention relates generally to solid supports with immobilized biopolymers and specifically to solid supports with immobilized unmodified biopolymers and methods of immobilizing unmodified biopolymers to solid supports.

2. Description of the Prior Art

Biopolymer synthesis and biopolymer analysis often require the attachment of biopolymers to solid supports. For example, organic and inorganic materials have been utilized for the solid phase synthesis of peptides, oligonucleotides and small organic molecules. The synthesis involves the stepwise addition of activated monomers such as amino acid derivatives or nucleotide derivatives to a growing oligomeric chain attached at one end to a solid support. At the completion of the synthesis, the newly synthesized biopolymers may be cleaved from the solid support and subsequently utilized in biochemical research or diagnostic applications or, alternatively, be utilized without cleaving the biopolymers from the solid support.

For biopolymer analysis, biopolymers may be attached to a solid support in several ways. In blotting techniques, native biopolymers are first captured onto a membrane and subsequently immobilized on the membrane by heat, radiation or chemical techniques. The immobilized biopolymers are then available for subsequent analyses, such as those associated with southern blotting applications and reverse hybridization analytical techniques.

Additionally, presynthesized or natural oligonucleotides have been immobilized by covalently attaching activated oligonucleotides to the solid support. Current methodology for the covvalent attachment of nucleic acids to solid supports (substrates) involves modification of the DNA (or RNA). For example, oligonucleotides are usually derivatized to a 5'-amino terminus, making the DNA more reactive for covalent attachment to an activated surface. Other methods of attachment have employed reactions with terminal phosphate groups or Sulfhydral groups with surface carbodiimide or other activation chemistries (see Lund et al, *Nucleic Acid Res.* 16:10861–80, 1988, Bischoff et al, *Analyt. Biochem.* 164: 336–344, 1987).

It is generally understood that reactive groups present within native polynucleotides are weak and therefore make for inefficient attachment. In addition, when native polynucleotides are exposed to highly reactive surface groups, excessive crosslinking may occur. This crosslink may prevent the attached nucleic acid from fully participating in hybridization. These conditions are most noticeable for short fragments of double-stranded DNA or oligonucleotides. Thus, oligonucleotides often have to be modified, for example, derivatized to a 5'-amino terminus, for an effective attachment. The 5' amino-linker allows selective binding of the amino-containing DNA to silylated slides through a Schiff's base reaction with aldehyde groups on the chip surface. The selectivity of amino-modified versus natural, unmodified DNA is about 10:1 for cDNAs and about 10,100:1 for single-stranded 15-mers. DNA molecules of intermediate lengths exhibit intermediate discrimination ratios. In addition, the 5' end attachment of the DNA to the chip via the amino group permits steric accessibility of the bound molecules during the hybridization reaction. Therefore, post-modification has been perceived as obligatory for attachment of, e.g., oligonucleotide probes for creation of arrays. Such post-modification processes require additional time-consuming steps at substantial costs.

Therefore, it is desirable to develop a more effective method for attaching biopolymers, particularly unmodified biopolymers to a solid support. It is particularly desirable to develop a method to directly attach unmodified biopolymers, such as polynucleotides, to a solid support.

SUMMARY OF THE INVENTION

The present invention is based on the discovery that both short and long fragments of single-stranded or double-stranded DNA may be efficiently attached to acyl fluoride activated supports directly without spacer arms and without modifying the polynucleotide. It is also based on the discovery that other biopolymers, such as protein A, antibodies, streptavidin, ect., may also be attached to a solid support without modifications to the biopolymers.

Accordingly, one aspect of the present invention provides a method of attaching unmodified biopolymers to a solid support. The method comprises the steps of:
  (a) providing unmodified biopolymers;
  (b) providing a solid support having at least one surface comprising pendant acyl fluoride lunctionalities, and
  (c) contacting the unmodified biopolymers with the solid support under a condition sufficient for allowing the attachment of the biopolymers to the solid support.

According to embodiments of the present invention, the biopolymers may be nucleic acids, polypeptides, proteins, carbohydrates, lipids and analogues thereof In one embodiment of the present invention, the biopolymer is a polynucleotide, and the polynucleotide may be synthesized oligonucleotide, amplified DNA, cDNA, single stranded DNA, double stranded DNA, PNA, RNA or mRNA. Also according to embodiments of the present invention, the solid support may be polymeric materials, glasses, ceramics, natural fibers, silicons, metals and composites thereof Another aspect of the present invention provides a method of analyzing a biopolymer target in a sample. The method comprises the steps of:
  (a) providing a solid support fabricated of a material having pendent acyl fluoride groups on at least one surface;
  (b) providing an agent that can form a complex with the biopolymer target, wherein the agent comprises a second biopolymer;
  (c) contacting the solid support with either the agent or the biopolymer target under a condition that allows the attachment of either the unmodified agent or the unmodified biopolymer to the solid support, wherein the agent and the biopolymer target are unmodified;
  (d) contacting the solid support attached with the unmodified agent with the biopolymer target, or contacting the solid support with the attached, unmodifed biopolymer target with the agent under a condition that allows the formation of a complex comprising the agent and the biopolymer target;
  (e) detecting and determining the presence of the complex as a measurement for presence or the amount of the biopolymer target contained in the sample.

A further aspect of the present invention provides a device comprising a plurality of unmodified biopolymer and a solid support. The solid support has at least one surface comprising pendant acyl fluoride functionalities, and the biopolymer is attached to the solid support by reaction with the pendant acyl fluoride functionalities.

The present invention is well-suited for use in creating polynucleotide arrays, such as sensor arrays and other array-based systems such as differential gene expression microarrays. The polynucleotide arrays may be used for the evaluation or identification of biological activity. The present invention may also be used in creating polynucleotide arrays for the purpose of polynucleotide sequencing. Further, the present invention may be used in hybridization assays and immunoassays.

The present invention provides many advantages. It allows for the attachment of unmodified biopolymers directly to a solid support. It thus simplifies and further increases the versatility of a process for creating biopolymer arrays.

There is both an economic advantage as well as a technical advantage to this invention. First, costly production of modified biopolymers, such as amino-modified DNA, may be avoided. Post-modification processing of oligonucleotides is time-consuming and can substantially increase costs by as much as two-fold. Second, the task of making arrays is greatly simplified, since post-modification processes are no longer required.

DESCRIPTION OF THE FIGURES

The above-mentioned and other features of this invention and the manner of obtaining them will become more apparent, and will best be understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

One aspect of the present invention provides a method of attaching unmodified biopolymers to a solid support. The method includes the steps of:

(a) providing unmodified biopolymers;

(b) providing a solid support having at least one surface comprising pendant acyl fluoride functionalities; and (c) contacting the unmodified biopolymers with the solid support under a condition sufficient for allowing the attachment of the biopolymers to the solid support.

The term "biopolymer" as used herein refers to nucleic acids, polynucleotides, polypeptides, proteins, carbohydrates, lipids and analogues thereof. As used herein, "polynucleotide" refers to a polymer of deoxyribonucleotides or ribonucleotides, in the form of a separate fragment or as a component of a larger construction. "Polynucleotide" as used herein may be DNA, RNA, a DNA analog such as PNA (peptide nucleic acid), or a synthesized oligonucleotide. The DNA may be a single or double-strand DNA, or a DNA amplified by PCR technique. The RNA may be a mRNA. The length of the polynucleotides may be 3 bp to 10 kb. In accordance with one embodiment of the present invention, the length of a polynucleotide is in the range of about 50 bp to 10 Kb, preferably, 100 bp to 1.5 kb. In accordance with another embodiment of the present invention, the length of a synthesized oligonucleotide is in the range of about 3 to 100 nucleotides. In accordance with a further embodiment of the present invention, the length of the oligonucleotide is in the range of about 15 to 20 nucleotides.

As used herein, "polypeptide" refers to a polymer of amino acids, wherein the α-carboxyl group of one amino acid is joined to the α-amino group of another amino acid by a peptide bond. A protein may comprise one or multiple polypeptides linked together by disulfied bonds. Examples of the protein include, but are not limited to, antibodies, antigens, ligands, receptors, etc.

It is a discovery of the present invention that biopolymers of the present invention may be attached to a solid support without any modification to the biopolymers. For example, in accordance with one embodiment of the present invention, biopolymers such as, but not limited to, polynucleotides, protein A, antibodies or streptavidin may be attached to a solid support without any modifications to the biopolymers.

For the purpose of the present invention, the solid support of the present invention may be any material capable of being derivatized to form acyl fluoride functionalities on at least one surface of the solid support. Examples of a solid support include, but are not limited to, polymeric materials, glasses, ceramics, natural fibers, silicons, metals and composites thereof.

In accordance with one embodiment of the present invention, a solid support of the present invention may be fabricated of a polymeric material having at least one surface with pendant acyl fluoride functionalities. The detailed description of the solid support and the methods of making the solid support are described in the pending U.S. application Ser. No. 08/797,222, entitled "Polymeric Reagents for Immobilizing Biopolymers," the relevant content of which is incorporated herein in its entirety by reference.

Briefly, polymeric materials suitable for fabricating solid supports can be any material capable of being derivatized to form acyl fluoride functionalities on at least one surface of the solid support. For example, polymeric materials with pendant carboxyl functionalities or polymeric materials capable of being modified to support carboxyl groups can be reacted with suitable reagents to form acyl fluoride functionalities. In one embodiment of the present invention, solid supports are fabricated of ethylene acrylic acid copolymers, ethylene methacrylic acid copolymers, or derivatized polypropylene. Those skilled in the art will recognize that polymeric materials capable of being derivatized to support carboxyl groups which in turn can be modified to provide surface acid fluoride functionalities include a wide range of materials. For example, aminated polypropylene reacted with a cyclic anhydride, e.g., succinic anhydride, to provide carboxyl groups suitable for converting to acyl fluoride is particularly useful.

Additional suitable polymeric materials include methylmethacrylate or methylacrylate saponified to expose a pendant carboxyl group:

Methyl(meth)acrylate

Still other polymeric materials easily derivatized to provide a reactive carboxyl group are hydrolyzed polyacrylonitrile or hydrolyzed polymethacrylonitrile:

(Meth)acrylonitrile

In accordance with the present invention, suitable reagents for forming acyl fluoride functionalities on at least one surface of the solid support broadly include carboxyl reactive fluoridating reagents. A most preferred reagent is (diethylaminosulphur) trifluoride (DAST) which reacts with pendant carboxyl groups in the following reaction:

Other reagents include cyanuric fluoride

-continued and tetramethylfluoroformadinium hexafluorophosphate:

Tetramethylfluoroformadinium hexafluorophosphate

In a most preferred embodiment of the present invention, ethylene acrylic acid copolymers or ethylene methacrylic acid copolymers formed into sheets having a thickness of about 0.5 mm are modified on at least one surface by exposing the surface to about a 5% solution of DAST for a period of several hours. After stopping the reaction, using dichloromethane and acetonitrile washes, the film is ready for use in immobilizing or synthesizing biopolymers as described below. Advantageously, it has been discovered that acyl fluoride activated polymeric materials are surprisingly stable at ambient conditions and, when stored in a cool dry environment, have unlimited shelf lives.

The solid supports of the present invention may also be prepared by methods comprising the steps of providing a solid support fabricated of ethylene acrylic acid copolymer or ethylene methacrylic acid copolymer and derivatizing at least one surface of the solid support by reacting the surface with an activating agent. Suitable activating agents are reagents capable of reacting with the acrylic or methacrylic carboxyl group to form reactive pendant functional groups, e.g., active acyl functionalities.

In accordance with another embodiment of the present invention, a solid support of the present invention may also be prepared by coating of an inert solid support with a polymeric material containing pendant acyl fluoride functionalities. For example, poly-glutamic acid carboxyl groups may be converted to acyl fluoride by a suitable fluorinating agent, such as DAST. The converted polymeric material may be used to coat a microtiter plate or other solid supports.

Because the solid support of the present invention is particularly useful in the preparation of biopolymer arrays for the evaluation or identification of biological activity, the solid support is preferably in the form of a device having at least one flat planar surface. The size of the solid support can vary and depends upon the final use of the immobilized biopolymers. Those skilled in the art will appreciate that arrays of biopolymers immobilized on miniaturized solid supports have been under development for many years. These solid supports can be measured in terms of $mm^2$ and can have numerous different immobilized biopolymers, each with different biopolymers attached to a different site specific location on the miniaturized solid support. Solid supports in the form of dip sticks are also within the scope of the present invention. As known in the art, dip sticks typically are rectangular in shape with each side measuring a few centimeters. On the other hand, large biopolymers such as polynucleotide arrays, utilized for sequencing whole genomes, may have dimensions measuring a meter or more.

In order to accommodate a number of different testing techniques including specialized testing equipment, suitable solid supports can also be molded into any of a variety of shapes. For example, it may be advantageous to mold a biopolymer array holder of the same polymeric material utilized to fabricate the solid support. In such a system the holder is the solid support and may be any shape, including one which is easily handled by an automated diagnostic system in which robotic arms move biopolymer arrays between reaction stations and detection stations. Preferably, when such a holder is the solid support, it incorporates a planar or continuous surface suitable for attaching biopolymers.

In accordance with one embodiment of the present invention, a solid support of the present invention may be made of a porous or non-porous material. In accordance with another embodiment of the present invention, a solid support of the present invention may be in a form of threads, sheets, films, gels, membranes, beads, plates and like structures. In accordance with a further embodiment of the present invention, a solid support may be fabricated from plastic in the form of a planar device having discrete isolated areas in the form of wells, troughs, pedestals, hydrophobic or hydrophilic patches, diecut adhesive reservoirs or laminated gaskets diecuts that form wells or other physical barriers to fluid flow. Examples of such a solid support include, but are not limited to, a microplate or the like.

The biopolymers of the present invention are attached to a solid support of the present invention by contacting the unmodified biopolymers with the solid support under a condition sufficient for allowing the attachment of the biopolymers to the solid support. A condition is sufficient if it allows the unmodified biopolymers to react with acyl fluoride of a solid support for covalently attaching the biopolymers to the solid support. While not wanting to be bound by the theory, it is believed that, under the conditions of the present invention, unmodified biopolymers may be attached to a solid support by displacement of the fluoride group contained in the solid support with a nucleophile of a biopolymer.

In accordance with one embodiment of the present invention, the step of contacting the acyl fluoride activated surface of the solid support under conditions which cause unmodified polynucleotides to react with acyl fluoride is accomplished by exposing the solid support surface to the unmodified polynucleotides in the presence of an aqueous buffer, preferably with a neutral or basic pH. Bringing the acyl fluoride functionalities into contact with the unmodified polynucleotides under neutral or basic pH conditions results in the attachment of the polynucleotides directly to the surface of the solid support. For the purpose of the present invention, a basic pH condition is a condition that has a pH greater than 8. A basic pH condition is sufficient if it allows the attachment of the polynucleotides to the solid support. In accordance with one embodiment of the present invention, the basic pH condition of the present invention has a pH of about 9 to 12. It should be understood that the basic pH condition may vary, depending on the method used. One skilled in the art can readily ascertain the basic pH condition of a particular attachment reaction in view of the disclosure of the present invention.

A solid support of the present invention may be contacted by unmodified biopolymers by methods that are known in the art. For examples, the contacting step may be carried out by jet printing, solid or open capillary device contact printing, microfluidic channel printing, silk screening, and a technique using printing devices based upon electrochemical or ectromagnetic forces. Alternatively, the contacting step may be carried out by spotting the unmodified biopolymers to the solid support.

For example, in one embodiment the solid support is exposed to unmodified polynucleotides by manual spotting. Examples of manual spotting include, but are not limited to, manual spotting with a pipettor or with a Biomek pin tool. In this case, the preferred aqueous base may be sodium bicarbonate-carbonate with a pH in the range of 9 to 10. In another embodiment, the solid support is exposed to unmodified polynucleotides by jet printing techniques. Thermal inkjet printing techniques utilizing commercially available jet printers and piezoelectric microjet printing techniques as described in U.S. Pat. No. 4,877,745 can be utilized to spot unmodified polynucleotides to solid supports. In this case, the aqueous base may be a LiCl salt solution with a pH of about 10 to 12.

It should be understood that the solid support of the present invention may be exposed to biopolymers by any methods as long as the biopolymers are put in contact with the solid support. It should also be understood that other aqueous buffer systems, which are not explicitly described here, may also be used in the present invention as long as the buffer system provides a sufficient condition that allows the attachment of biopolymers to the solid support once they are in contact with each other.

In accordance with embodiments of the present invention, the concentration of unmodified biopolymers contained in aqueous solutions may vary, depending on the type of molecule, the molecule size, the molecule structure, and other factors that may influence solubility of the molecules. For example, when the attached polymers are polynucleotides, preferably they are in the range of 5 nM to 40:M. More preferably, they are in the range of 5 nM to 5:M.

In accordance with the present invention, it is preferable, subsequent to the attachment of biopolymers to solid supports, to "block" the nonreacted acyl fluoride functionalities from further unwanted reactions. For the purpose of the present invention, the residual acyl fluoride groups contained in the solid support may be blocked by any chemicals that can inactivate the remaining surface reactive groups. For example, unreacted acyl fluoride functionalities may be reacted with ammonium hydroxide to form carboxamide or with ethanol to form esters. Those skilled in the art will recognize, however, that a host of blocking reactions are possible.

As mentioned above, many applications for utilizing immobilized biopolymers require that biopolymers be immobilized at site specific locations on a solid support surface. In order to prepare ordered arrays of biopolymers, including grids and 1×n arrays of immobilized biopolymers with each biopolymer located at site specific locations, a preselected site on the surface of the activated polymeric material is exposed to a solution of the desired unmodified biopolymers. In accordance with the present invention, this can be accomplished manually by applying an amount of unmodified biopolymer solution to a preselected location on the solid support. Alternatively, thermal inkjet printing techniques utilizing commercially available jet printers and piezoelectric microjet printing techniques as described in U.S. Pat. No. 4,877,745 can be utilized to spot selected solid support surface sites with selected unmodified biopolyers.

In accordance with one embodiment of the present invention, at least 1 to about 1536 different unmodified biopolymers may be attached to at least 1 to about 1536 discrete isolated areas in a solid support of the present invention Attachment of unmodified biopolymers to acyl fluoride activated solid supports is well-suited for use in the construction of genosensors and other array-based systems such as differential gene expression micro-arrays. A solid support with attached unmodified biopolymers of the present invention may also be used as a device for performing a ligand binding assay or for performing a hybridization assay by either reverse hybridization (probes atttached) or southern blot (target attached). Such a device may also be used in an immunoassay.

Accordingly, one aspect of the present invention provides a method for analyzing a biopolymer target in a sample. The method comprises the steps of:

(a) providing a solid support fabricated of a material having pendant acyl fluoride groups on at least one surface;

(b) providing an agent that can form a complex with the biopolymer target, wherein the agent comprises a second biopolymer;

(c) contacting the solid support with either the agent or the biopolymer target under a condition that allows the attachment of either the unmodified agent or the unmodified biopolymer to the solid support, wherein the agent and the biopolymer target are unmodified;

(d) contacting the solid support attached with the unmodified agent with the biopolymer target, or contacting the solid support with the attached, unmodifed biopolymer target with the agent under a condition that allows the formation of a complex comprising the agent and the biopolymer target;

(e) detecting and determining the presence of the complex as a measurement for the presence or the amount of the biopolymer target contained in the sample.

For the purpose of the present invention, either the target biopolymer or the agent for the target biopolymer may be bound to a solid support of the present invention. For examples, in southern blot or northern blot, target biopolymers are first bound to a solid support. Probes, preferably labeled, are used to contact the solid support to detect the existence of the target biopolymers. To the contrary, in ligand binding assays or affinity purification assays, probes are preferably bound to a solid support first.

For the purpose of the present invention, an agent of the present invention comprises a biopolymer that can recognize the target biopolymer and bind to the target biopolymer. An agent may comprise a biopolymer selected from a group consisting of nucleic acids, polypeptides, proteins, carbohydrates, lipids and analogues thereof. For example, when the target biopolymer is a polynucleotide, the agent may comprise a polynucleotide that is complimentary to the target polynucleotide. When the target biopolymer is a receptor or a ligand, the agent may comprise a ligand or a receptor that respectively recognizes the biopolymer and binds to the biopolymer. When the target biopolymer is an antigen, the agent may comprise an antibody that recognizes the antigen, or vise versa. In addition, the target biopolymers may be labeled with a binding agent. In this case, the agent may comprise a binding agent that recognizes the labeled biopolymers. For example, a biopolymer of the present invention may be labeled with biotin. In this case, the agent may comprise streptavidin which can bind to biotin of the target biopolymer.

For the purpose of the present invention, a condition is sufficient if the agent can bind to the target biopolymer to form a complex. Such a condition may vary, depending on the type of molecules and the type of bindings. One skilled in the art can readily determine the suitable conditions for binding in view of the teaching of the present invention.

In accordance with embodiments of the present invention, both the target biopolymers or agents of the present invention may be labeled with a reporter molecule. Examples of reporter molecules include, but are not limited to, dyes, chemiluminescent compounds, enzymes, fluorescent compounds, metal complexes, magnetic particles, biotin, haptens, radio frequency transmitters, and radioluminescent compounds. One skilled in the art can readily determine the type of reporter molecule to be used once the type of target biopolymers is determined.

Another aspect of the present invention also provides a device for performing hybridication assays, immunoassay or other assays. A device of the present invention comprises a plurality of unmodified biopolymers and a solid support. The solid support has at least one surface comprising pendant acyl fluoride functionalities, and the biopolymer is attached to the solid support by reaction with the pendant acyl fluoride functionalities.

For the purpose of the present invention, the attached biopolymers may be the same or different. If the biopolymers are different, preferably they are located in discrete, isolated areas of the solid support to form arrays. For example, a solid support may be a microplate. Different biopolymers may be attached to different wells of the microplate for forming arrays. In acordance with one embodiment of the present invention, at least 1 to 1536 unmodified biopolymers, such as probes, may be attached to at least 1 to 1536 wells of a microplate.

The solid support of the device, such as a microplate, may be surface treated with acyl fluoride functionalities, and then biopolymers may be attached to the solid support by reaction with the pendant acyl fluoride functionalities. Alternatively, biopolymers of the present invention may be printed onto the surface of a plastic disk containing pendant acyl fluoride functionalities, and the disk is then inserted into the bottom of the microplate well.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Hybridization of cDNA to Printed Arrays of Unmodified Polynucleotides Printing of Primer Arrays Unmodified oligonucleotide primers used for amplification of actin, G3PDH, p53 and TNF alpha genes were prepared by dilution into saturated LiCl, pH 12 stock solution at approximately saturated LiCl: water (60:25 v/v). The resulting printing ink was at a final concentration of 10 $\mu$M oligonucleotide. Using a BioDot Dispenser System, primers were deposited by jetting 12.5 nL of each ink onto a molded piece (Biotip) of acyl fluoride activated ethylene methacrylic acid copolymer (EMA) to form an array. The 9×8 array consisted of 9 replicate spots for each 3' & 5' primer pair for the 4 genes (9×2×4=72 spots). Following printing, the arrays were dried overnight under vacuum and remaining surface reactive groups inactivated (blocked) for two hours in ethanol. The arrays were rinsed briefly with water in preparation for use in hybridization.

Printing of cDNA Probe Arrays

In a similar manner, double-stranded DNA probes were printed onto acyl fluoride activated substrates. The cDNA was amplified by PCR of $1^{st}$ strand DNA without incorporation of biotin label. The cDNA PCR products (cDNA amplicons) were purified using gel filtration spin-columns (Xtreme, Pierce Chemical) to remove primers, dNTPs, along with cofactors and Taq enzyme. The amplicons were eluted from the columns with deionized water and prepared for printing by dilution into 1M LiCl, pH 12 to yield an ink of LiCl: water (1:1 v/v) at a final cDNA concentration of 5 nM. The same spotting procedure was used as described for primer printing, except in this case the array consisted of nine replicates of six genes (9×6=54 spots): actin cDNA, beta microglobulin cDNA, G3PDH cDNA, p53 cDNA, transferrin cDNA and TNF alpha cDNA. The droplet size dispensed was approximately 16 nL.

Hybridization

Biotips with cDNA arrays attached were denatured for 15 minutes in 200 μL denaturant (0.15 M NaCl, 0.5M NaOH), then rinsed in stringency buffer (2×SSC, 0.01% SDS, pH 7.0) just prior to hybridization. In the case of Primer Array Biotips, no denaturation step was used. Biotin-labeled PCR products of actin, G3PDH, p53 and TNF alpha derived from a $1^{st}$ strand cDNA pool (liver) were prepared for hybridization to the Primer Arrays or cDNA Arrays as follows: 10 μL PCR solution was diluted with 10 μL water and 50 μL denaturant added. The solution was incubated for 10 minutes at ambient temperature followed by the addition of 150 μL of neutralization buffer (0.3M Tris, pH 7.5, 2.4×SSC, 0.02% SDS). After mixing, the solution was placed in well of a 24-well polypropylene cell culture plate and the Biotip immersed. Hybridization was allowed to proceed for 60 minutes at 25° C. for cDNA Arrays of 60° C., 60 minutes for Primer Arrays with shaking in a humidified chamber. The Biotips were then removed from the hybridization solution and placed in another well containing 2×SSC, 0.01% SDS for a stringency rinse (at the same temperature used for hybridization) for 10 minutes. Upon a final rinse in the above stringency buffer, the Biotip was blotted to remove excess solution and placed in streptavidin-alkaline phosphatase conjugate for 30 minutes at ambient temperature. Following extensive rinsing in stringency buffer, the Biotip was again blotted, then placed in ELF reagent (fluorescent substrate for alkaline phosphatase, Molecular Probes, Inc.) for signal development. The signal was allowed to develop for 30 minutes. Following a brief water rinse, the array signal was read using a CCD camera system.

Results

Figure 1A:
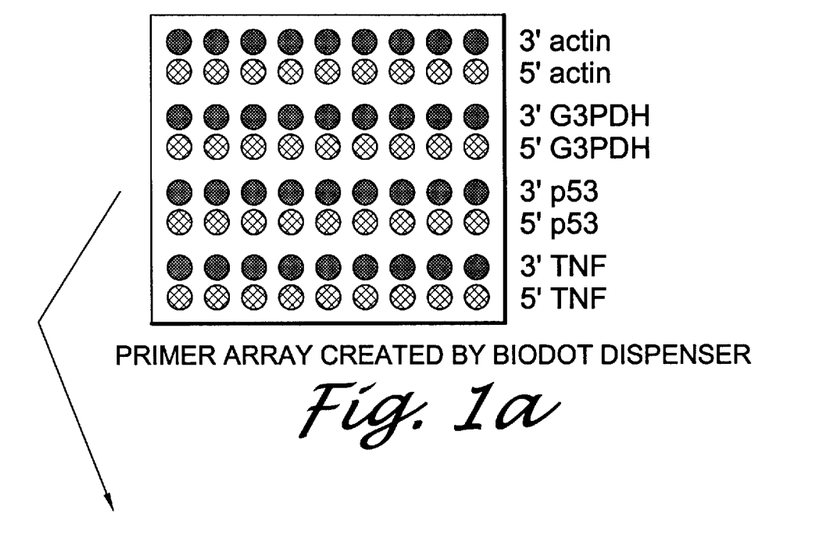
FIG. 1a shows the hybridization results of labeled target cDNA from actin, G3PDH, p53 and TNF with their corresponding solid-phase primers.
Figure 1B:
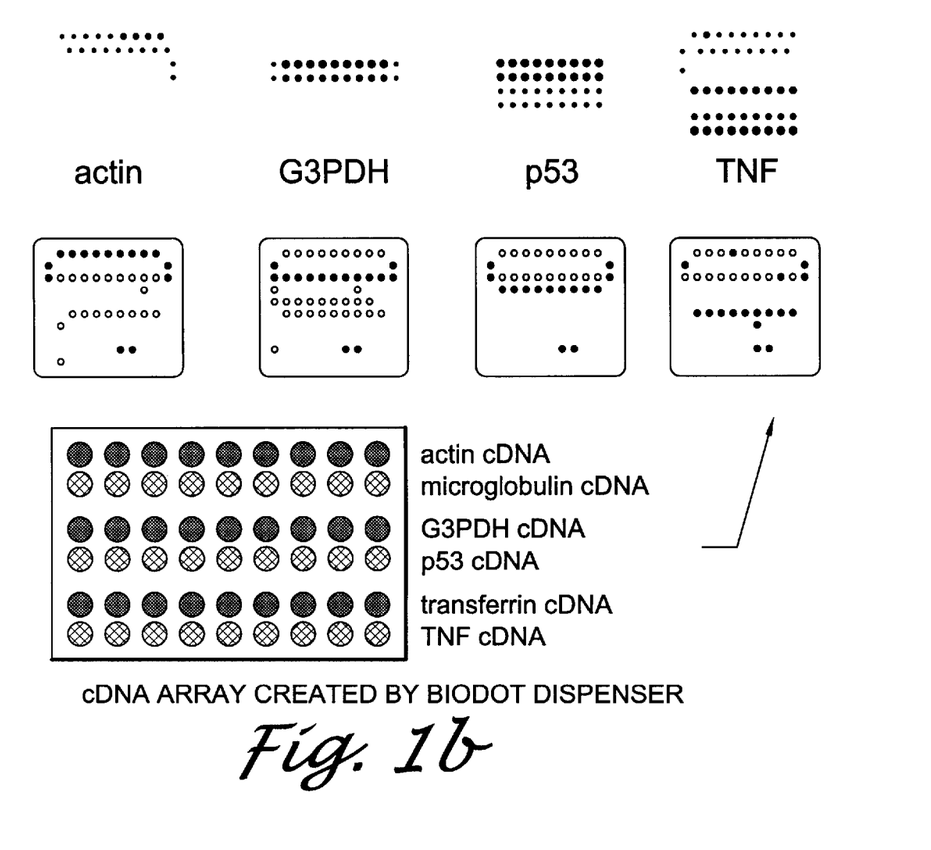
FIG. 1b shows the hybridization results of labeled cDNA targets with their corresponding probe cDNA immobilized by the same process.

As shown in FIG. 1a, labeled target cDNA from actin and G3PDH hybridized specifically to their corresponding solid-phase primers, while cDNA from p53 showed cross-hybridization to G3PDH primers. TNF alpha also cross-hybridized to 3' primers of actin and p53. These results are similar to those using labeled cDNA targets hybridized to probe cDNA immobilized by the same process (FIG. 1b)

EXAMPLE 2

Hybridization of cDNA Targets to Manually Spotted Arrays of Unmodified Oligonucleotide Primer Pairs Manual Spotting of Primer Arrays Oligonucleotide primers for the amplification of actin, p53 and TNF alpha genes were prepared at the following concentrations for spotting in 0.5 M sodium bicarbonate buffer, pH 9:

| Primer | μM (final conc.) |
| --- | --- |
| Actin 3' | 5.01 |
| Actin 5' | 5.00 |
| P53 3' | 3.73 |
| P53 5' | 3.83 |
| TNF 3' | 3.80 |
| TNF 5' | 3.70 |

Figure 2:
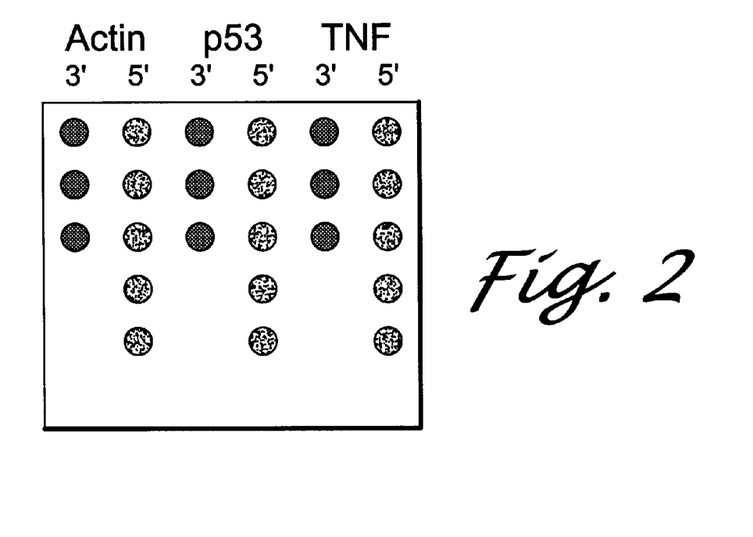
FIG. 2 shows an array pattern created by manual pipettor spotting.

Approximately 1 μL drop of each of these were spotted onto an acyl fluoride activated plastic support (EMA) using a manual pipettor creating an array similar to the pattern shown below in FIG. 2.

After spotting, the arrays were incubated at 25° C., 1 hour in a humidified chamber. They were then removed from the chamber and allowed to air-dry 25 minutes at ambient temperature, followed by an additional drying at 30° C. for 10 minutes. The plastic supports were then immersed in ethanol for 60 minutes to block residual reactive surface groups, followed by a final 10-minute soak in deionized water.

Hybridization

Biotin-labeled PCR products of actin, p53 and TNF alpha derived from a $1^{st}$ strand cDNA pool (liver) were prepared for hybridization to the Primer Arrays as follows: 10 μL PCR solution was diluted with 10 μL water and 30 μL denaturant added. The solution was incubated for 10 minutes at ambient temperature followed by the addition of 150 μL of nuetralization buffer. After mixing, the solution was placed in a well of a 24-well polypropylene cell culture plate and the Biotip immersed. Hybridization was allowed to proceed for 60 minutes at 60° C. with shaking in a humidified chamber. The Biotip was then removed from the hybridization solution and placed in another well containing 2×SSC, 0.01% SDS for a stringency rinse at 60° C. for 10 minutes. Upon a final rinse in the above stringency buffer, the Biotip was blotted to remove excess solution and placed in streptavidin-alkaline phosphatase conjugate for 30 minutes at ambient temperature. Following extensive rising in stringency buffer, the Biotip was again blotted, then placed in ELF reagent for signal development. The signal was allowed to develop for 30 minutes. Following a brief water rinse, the array signal was read using a CCD camera system.

Results

Figure 3:
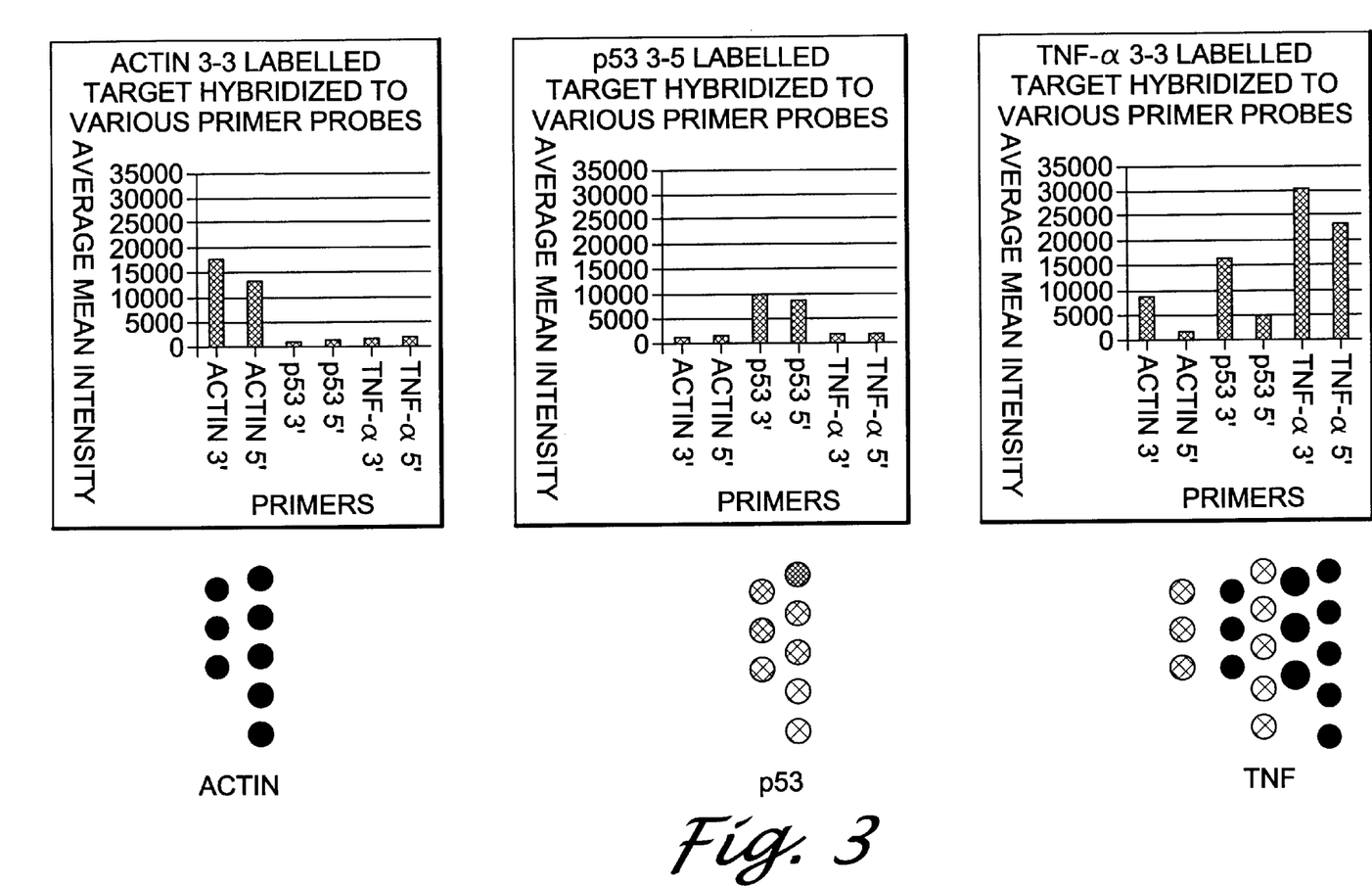
FIG. 3 shows the hybridization results of cDNA targets with manually spotted arrays of unmodified oligonucleotide primer pairs.

FIG. 3 shows the results of the hybridization. The biotin-labeled cDNA targets hybridized specifically to their complementary immobilized primer probes. Actin and p53 targets showed little cross-hybridization to non-complementary primer probes tethered to the surface. However, TNF target exhibited significant cross-hybridization, especially to the 3' primers.

EXAMPLE 3

Hybridization of Biotin-labeled Oligonucleotide Targets to Printed Arrays of Amino Modified and Unmodified Oligonucleotide Probes Printing of Fib Probe Arrays 5'-amino modified (Fib-a) and unmodified oligonucleotide (Fib) probes were prepared by dilution into saturated LiCl, pH 12 to yield saturated LiCl: water (60:25 v/v) printing ink at final concentrations from 10 μM to 40 μM for Fib; and 10 μM for Fib-a. Using a BioDot Dispenser System, nine replicate spots of each probe solution were deposited by jetting 16 nL of each ink onto a molded piece (Biotip) of acyl fluoride activated EMA to form an array. Following printing, the arrays were dried overnight under vacuum and remaining surface reactive groups inactivated (quenched) for two hours in ethanol. The arrays were briefly rinsed with water in preparation for use in hybridization.

The Fib Probe, 5'-CGGCTGGACACGCTTCTGTAG-3', is identified as SEQ ID No:1. The Fib-a Probe, 5'-NH2-CGGCTGGACACGCTTCTGTAG-3', is identified as SEQ ID NO:2. The Fib Target, 5'-Biotin-CTACAGAAGCGTGTCCAGCCG-3', is identified as SEQ ID NO:3.

Hybridization

Fib target (100 nM, final conc.) was prepared by mixing 20 μL of a 1 μM stock solution with 30 μL of denaturant. The target was held under denaturing conditions for 10 minutes at ambient temperature followed by the addition of 150 μL of neutralization buffer. The Biotip was immersed in the solution held in a well of a 24-well polypropylene microtiter late which was in turn placed in a humidified chamber for 60 minutes at 25 C. Following a 10-minute rinse in 2×SSC, 0.01% SDS, pH 7.0 stringency buffer, the Biotip was incubated for 30 minutes at ambient temperature in a steptavidin-alkaline phosphatase conjugate solution prepared in stringency buffer. The Biotip was rinsed 2× with stringency buffer to remove unbound conjugate; and then immersed in ELF reagent for signal development for 30 minutes. Following a brief water rinse, the Biotip array signal was read using a CCD camera system.

Results

Figure 4:
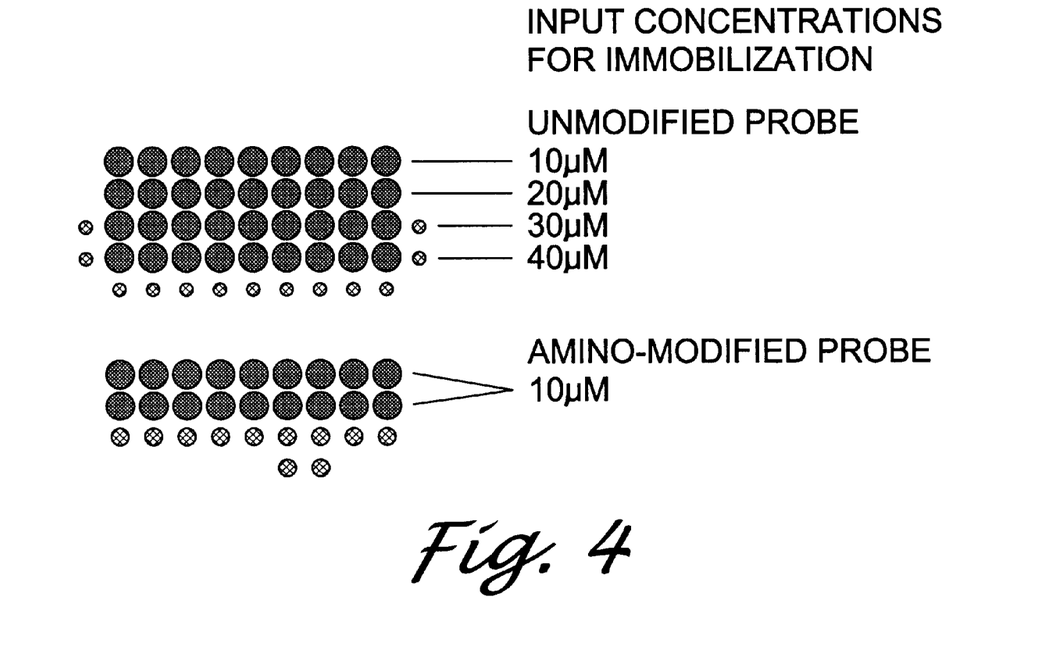
FIG. 4 shows the hybridization results of the biotinylated Fib target oligonucleotide with both amino-modified and unmodified complementary probes of the array.

FIG. 4 shows that the biotinylated Fib target oligonucleotide hybridized to both amino-modified and unmodified complementary probes of the array.

Figure 5:
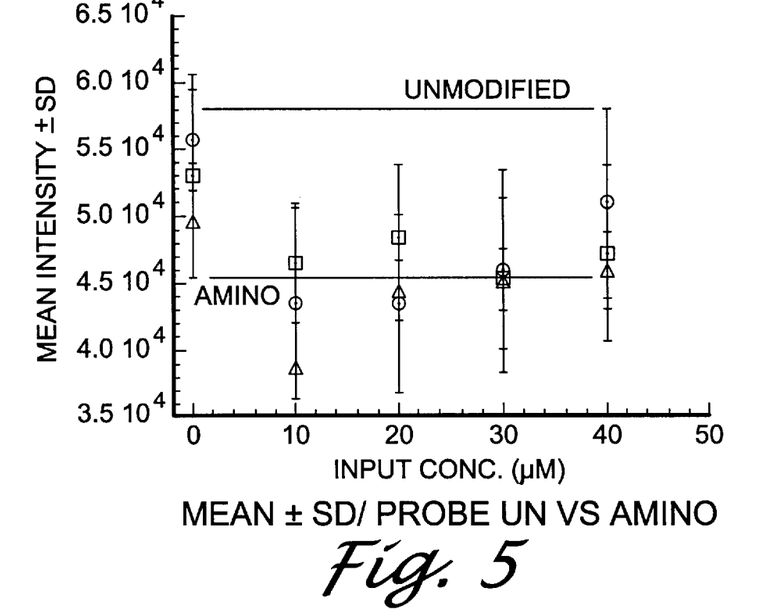
FIG. 5 is an image analysis of the mean signal intensities for each probe spot within the array.

Image analysis of the mean signal intensities for each probe spot within the array was conducted for three separate Biotip arrays. FIG. 5 shows that amino-modified probe and unmodified probe hybridizations were of approximately the same level when considering the range of values estimated from the standard deviation.

EXAMPLE 4

Preparation and Characteristics of cDNA Arrayed onto Acyl Fluoride Activated Polypropylene Films Activation of Polypropylene Films Polypropylene film was surface aminated by radio frequency plasma (U.S. Pat. No. 5,554,501) and amine functionalities converted to carboxyl groups by reaction with succinic anhydride. The acyl fluoride activation was accomplished using the DAST reagent as described previously in the copending U.S patent application Ser. No. 08/797,222. Acyl fluoride activated polypropylene film was stored dry under argon at −20 C until needed.

Printing of cDNA Arrays

Unmodified cDNA from pcr amplification of $_1$st strand cDNA (liver tumor) was purified by gel filtration spin column (XTreme, Pierce Chemical) to remove primers, dNTPs, cofactors and Taq enzyme. The purified cDNA was eluted from the columns with water, then diluted into 0.5 M sodium bicarbonate buffer, pH 9 for coupling. A Biomek 2000™ robotic system equipped with a 384-pin HDRT system was used to print cDNA solutions onto the substrate. A set of BAPA markers, 5-(Biotinamido)pentylamine (Pierce Chemical), were also printed at both ends of the film, thereby flanking the tethered cDNAs. BAPA, which binds streptavidin-enzyme conjugate independently of hybridization, serves as an internal control for assay robustness. Following printing, the films were dried at 35 C for 15 minutes and then immersed in ethanol for two hours to block residual surface reactive groups. The films were briefly rinsed in deionized water and allowed to air dry. The 8 cm×12 cm film was sectioned into 12 pieces with each strip containing two copies of a 3×3 replicate of each cDNA along with six copies of 3×3 replicates of the BAPA marker. The resulting cDNA Array film strips were stored dry at −20° C. or room temperature prior to hybridization.

Hybridization

For hybridization, each film strip was denatured for 15 minutes in 150 μL of denaturant dispensed onto a glass microscope slide. Following the denaturation step, the film strips were removed from the slide and briefly rinsed in stringency buffer to remove residual denaturant. A mixture of biotin-labeled pcr products of actin, G3PDH and TNF alpha derived from a $1^{st}$ strand cDNA pool (liver tumor) were prepared for hybridization in a 15 mL polypropylene tube as follows: 15 μL of each cDNA pcr solution was mixed and then diluted with 180 μL water. Then 337.5 μL of denaturant was added. Denaturation was allowed to proceed for 10 minutes at ambient temperature followed by the addition of 1687.5 μL of neutralization buffer to the tube. A 150 μL aliquot was transferred onto glass microscope slides and the film arrays placed over the solution with the DNA side down. Hybridization was allowed to proceed for 60 minutes at 60 C with shaking in a humidified chamber. The film strips were then removed from the hybridization solution, transferred to 50 mL polypropylene screw cap culture tubes and the films first rinsed briefly, then immersed in 40 mL of 2×SSC, 0.01% SDS buffer preheated to 60 C for a stringency rinse at 60 C for 10 minutes. Upon a final rinse in the above stringency buffer, the films were blotted to remove excess solution and placed on glass microscope slides containing a solution of streptavidin-alkaline phosphatase conjugate for 30 minutes at ambient temperature. Following extensive rinsing in stringency buffer, the films were again blotted, then placed in ELF reagent for signal development. The signal was allowed to develop for 30 minutes. Following a brief water rinse, the array signal was read using a CCD camera system.

Results

Figure 6:
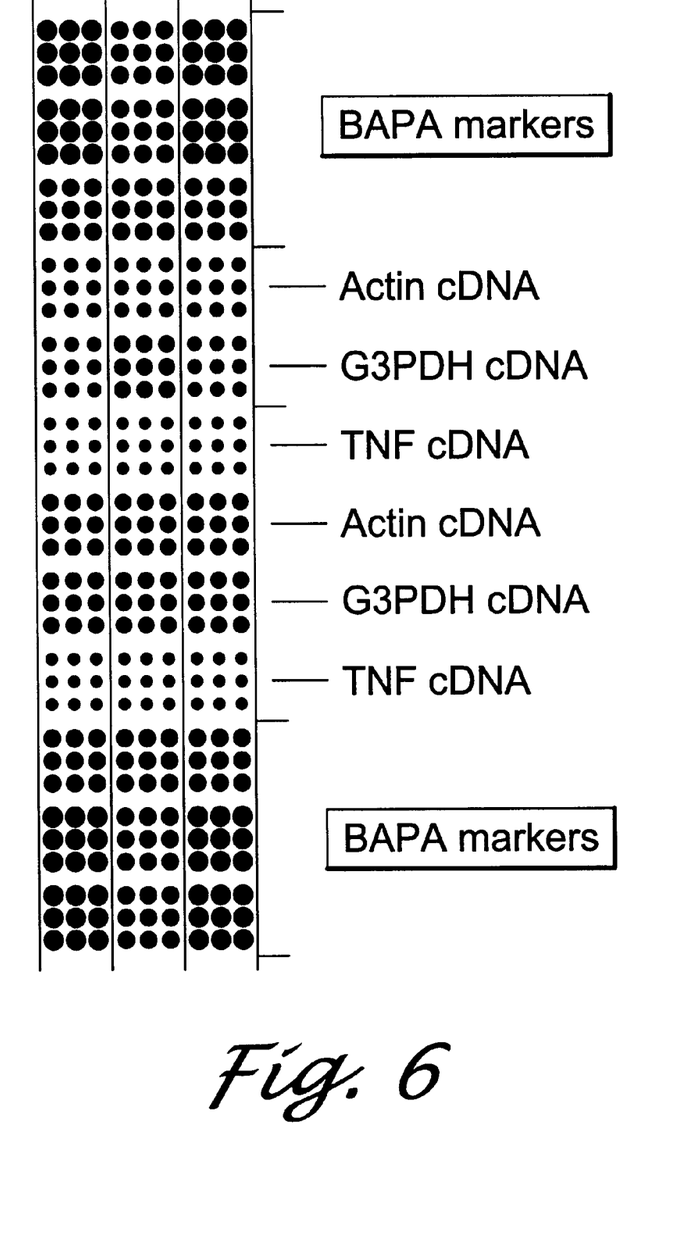
FIG. 6 shows Biomek HDRT printing of cDNA and BAPA markers onto acyl fluoride activated polypropylene films.
Figure 7:
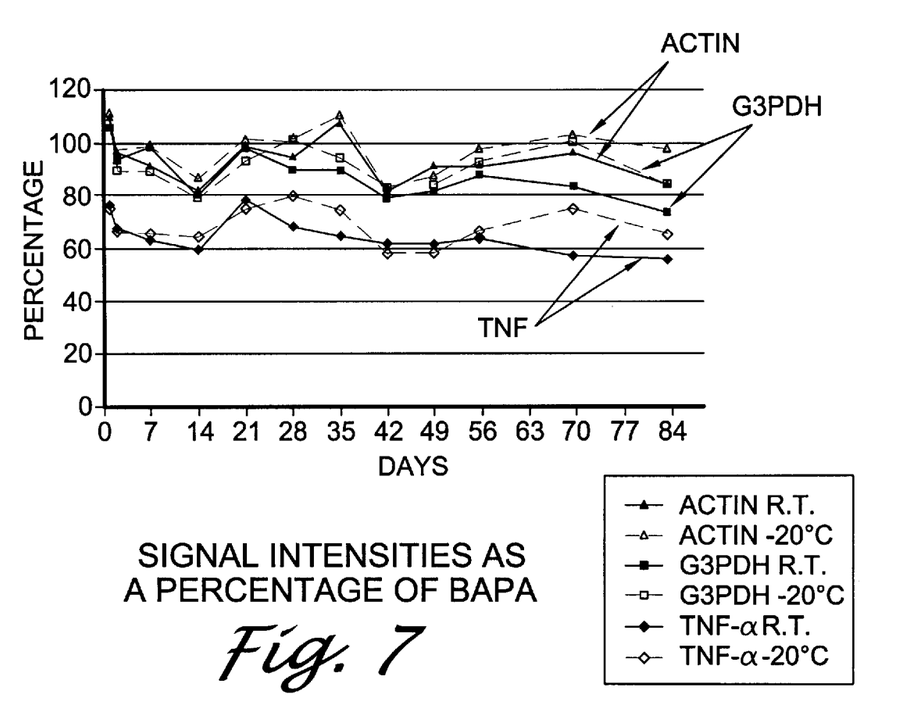
FIG. 7 shows the stability of polypropylene-based cDNA arrays.
Figure 8:
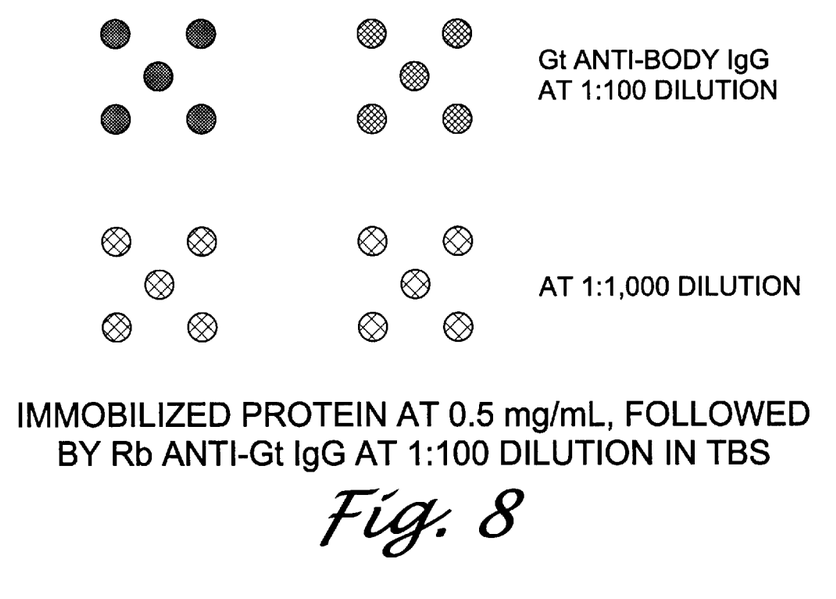
FIG. 8 shows the immobilization of Protein A.

An array of cDNA and BAPA markers was successfully printed onto acyl activated polypropylene films as determined by hybridization of a mixture of the corresponding cDNAs (FIG. 6). FIG. 6 shows Biomek HDRT printing of cDNA and BAPA markers onto acyl floride activated polypropylene films (day 7 hybridization to 3 separate film strips). Storage of film arrays, either at ambient temperature or at −20° C., did not adversely affect hybridization over an approximate three-month period (FIG. 7). FIG. 7 shows the stability of polypropylene-based cDNA arrays. Signal intensities were normalized to the BAPA market intensities to account for differences in assay conditions over the extended period. All cDNA probes maintained hybridization efficiency under either temperature storage condition. The TNF signal was consistently lower than the BAPA marker signals, while the remaining cDNA hybridization signals remained approximately at the same intensity as the BAPA markers.

EXAMPLE 5

Protein Immobilizations

Proteins, Buffers and other Reagents
1. Biotinylated Alkaline Phosphatase: Pierce Immunopure® (lot #95120774)
2. Rabbit anti-goat IgG (H+L): Zymed Laboratories, South San Francisco, Calif. (lot #2112098)
3. Goat anti-biotin IgG: Sigma Chemical Co. (lot #116H8842), affinity isolated antibody; reconstituted to 1 mg/mL in PBS.
4. Protein A: Zymed Laboratories, South San Francisco, Calif. (lot #21212416); reconstituted 5 mg in 2 mL deionized water (2.5 mg/mL).
5. Streptavidin (from, *S. avidini*): Zymed Laboratories, South San Francisco, Calif. (lot #70536128); reconstituted 5 mg in 1 mL deionized water (5 mg/mL).
6. Casein: Hammersten (lot #BDH44020)
7. Coupling buffer: 1 M sodium carbonate, pH 9 or 10 diluted to 0.8 M with protein solution
8. ELF® Reagent (ELF®-97 Endogenous Phosphatase Detection Kit): Molecular Probes, Eugene, Oreg. (lot #6771)
9. High salt buffer: 1.0 M Tris, 1.5 M NaCl, pH 7.5 (Digene Neutralizing Buffer); Digene Diagnostics, Beltsville, Md. (lot #0094MX95)
10. Quenching/Blocking buffer: 1 mg/mL casein,50 mM Carbonate, 0.15 M NaCl, pH 8.5
11. TBS: 50 mM Tris, 0.15 M NaCl, pH 7.5

Methods

Imobilization of Proteins on Biotips

Proteins (Protein A, streptavidin, rabbit anti-goat IgG) were diluted into 1 M carbonate buffer, pH 9 or 10, to a concentration of 0.5–1.0 mg/mL. The protein solution was applied to the surface of acyl fluoride activated plastic Biotips in 0.5 μL drops. The tips were incubated in a high humidity chamber at 25° C. for 1 hr. They were then removed from the chamber and allowed to air dry completely (~15 min) before being placed in the quenching/blocking solution. The tips were quenched by placing in 1.0 mL solution in a 24-well plate and vortexing vigorously for a minimum of 30 min. After quenching, the tips were rinsed with deionized water for 10 min with shaking and air dried.

Detection of Alkaline Phosphatase with ELF Reagent

For each tip, 50 μL ELF reagent is prepared according to the Molecular Probes procedure (ie., 19 parts Reagent B plus 1 part Reagent A) and applied to the surface of the tips. The tips with ELF reagent were incubated for 30 min in a box partially filled with water to maintain humidity. Afterwards, the tips are rinsed three times with deionized water. The tips are photographed under UV light at 365 nm excitation with a 520 nm lens filter. Exposure time for the CCD camera was typically 10 sec.

Experimental Results

Immobilization of Protein A on Biotips

Signal Development & Detection: Inicubated Rb anti-Gt IgG, 1:100 in TBS for 1 hr, followed by Gt anti-biotin IgG in TBS for 1 hr, and then biotin-AP conjugate in 2×SSC, 0.01% SDS for 1 hr. Image developed with ELF. The immobilized Protein A was demonstrated to be functional in it's capture of the rabbit (Rb) antibody in the above sandwich-based immunoassay.

Immobilization of streptavidin on Biotips

Prepared at 1 mg/mL in 0.8 M carbonate, pH 9. Incubated for 1 hr at room temperature. Quenched for 45 min on Vortexer with different blocking agents (at 1 mg/mL).

Figure 9:
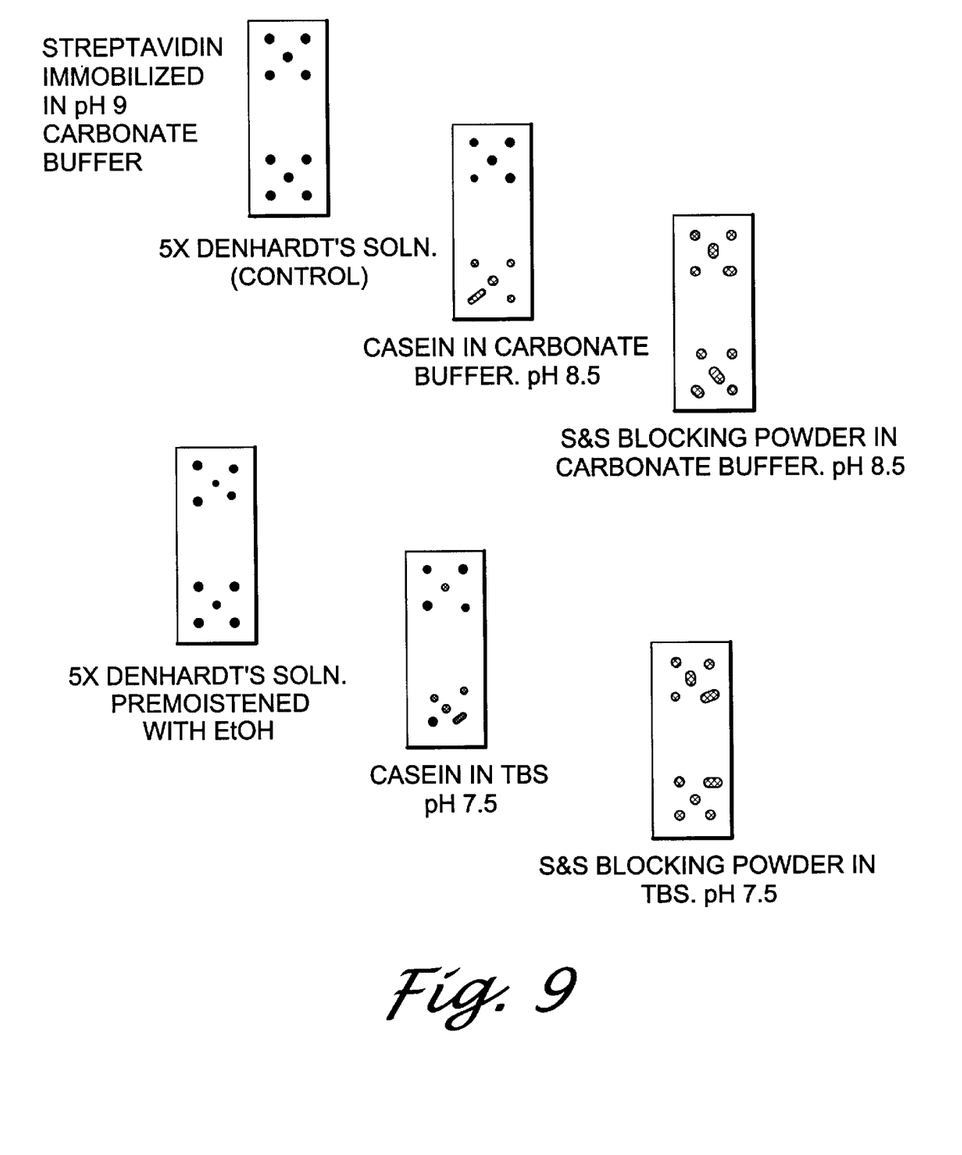
FIG. 9 shows the immobilization of streptavidin.

Signal Development & Detection:

Incubated biotinylated alkaline phosphatase diluted 1:100 in 2×SSC, 0.01% SDS buffer for 1 hr. ELF reagent incubation for 30 min. at room temperature. Immobilized streptavidin was demonstrated to be functional in the specific capture of a biotinylated enzyme under a variety of blocking conditions aimed at reducing non-specific binding. (FIG. 9)

Immobilization of Antibody on Biotips

Figure 10:
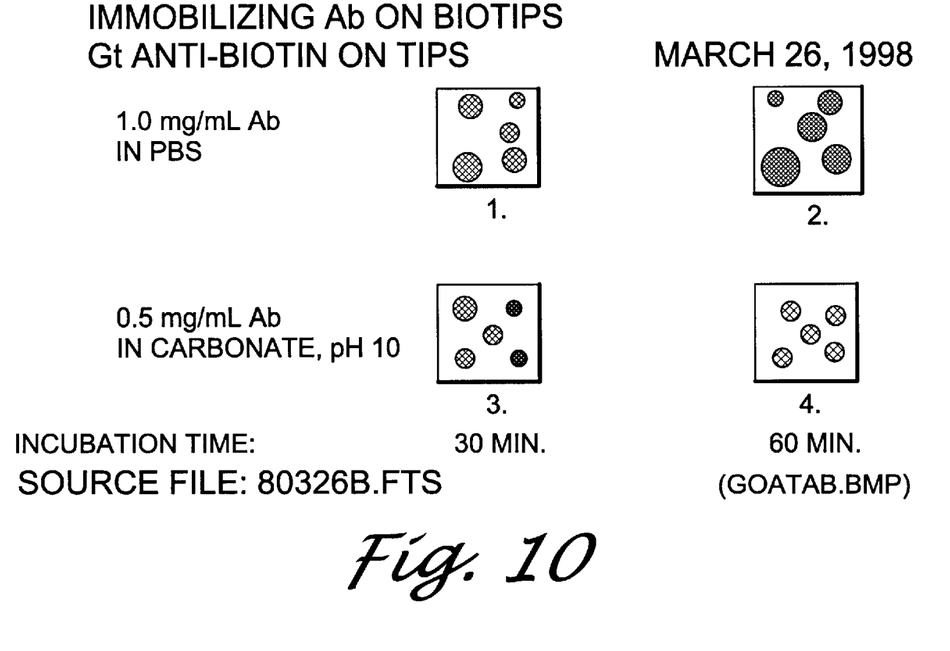
FIG. 10 shows the immobilization of Gt anti-biotin IgG antibody.

Gt anti-biotin IgG immobilized on Biotips in the following:
1. 1.0 mg/mL in PBS, pH 7.2 incubated for 30 min
2. 1.0 mg/mL in PBS, pH 7.2 incubated for 60 min
3. 0.5 mg/mL in 0.8 M carbonate, pH 10 incubated for 30 min
4. 0.5 mg/mL in 0.8 M carbonate, pH 10 incubated for 60 min Signal Development & Detection Incubation with biotin-alkaline phosphatase conjugated diluted 1:100 in high salt buffer for same time as antibody incubation. Development with ELF reagent for 30 min. at room temperature. The antibody, goat anti-biotin IgG, was successfully immobilized at both pH 7.2 and pH 10, as demonstrated by specific capture of biotin labeled reporting enzyme (alkaline phosphatase) (FIG. 10).

The foregoing is meant to illustrate, but not to limit, the scope of the invention. Indeed, those of ordinary skill in the art can readily envision and produce further embodiments, based on the teachings herein, without undue experimentation.

SUMMARY OF SEQUENCES

SEQ ID NOS:1, 2, and 3 are nucleotide sequences of oligonucleotides Fib Probe, Fib-a Probe, and Fib Target, respectively.

What is claimed is:

1. A method of attaching unmodified biopolymers to a solid support comprising the steps of:
   (a) providing unmodified biopolymers;
   (b) providing a solid support having at least one surface comprising pendant acyl fluoride functionalities; and
   (c) contacting the unmodified biopolymers with the solid support under a condition sufficient for allowing a direct attachment of the unmodified biopolymers to the solid support, in the absence of a spacer arm or a modification of the bionolymers.

2. The method of claim 1, wherein biopolymers are selected from a group consisting of nucleic acids, polypeptides, proteins, carbohydrates, lipids and analogues thereof.

3. The method of claim 2, wherein the biopolymers are selected from a group consisting of polynucleotides, protein A, antibodies, and streptavidin.

4. The method of claim 3, wherein the biopolymer is a polynucleotide.

5. The method of claim 4, wherein the polynucleotide is selected from a group consisting of synthesized oligonucleotide, amplified DNA, cDNA, single stranded DNA, double stranded DNA, PNA, RNA, and mRNA.

6. The method of claim 4, wherein the length of the polynucleotide is in the range of about 3 bp to 10 kb.

7. The method of claim 6, wherein the length of the polynucleotide is in the range of about 100 bp to 1.5 kb.

8. The method of claim 5, wherein the length of the oligonucleotide is in the range of about 3 to 100 nuecleotides.

9. The method of claim 8, wherein the length of the oligonucleotide is in the range of about 15 to 20 nuecleotides.

10. The method of claim 1, wherein the solid support is selected from a group consisting of polymeric materials, glasses, ceramics, natural fibers, silicons, metals and composites thereof.

11. The method of claim 1, wherein the solid support is a polymeric material selected from a group consisting of ethylene acrylic acid, ethylene methacrylic acid, carboxylated polyuinylidene floride, carboxylated polypropylene or carboxylated polyethylene, and copolymers thereof.

12. The method of claim 1, wherein the step (b) comprises a step of coating an inert solid support with a polymeric material to obtain the solid support having at least one surface comprising pendant acyl fluoride functionalities, wherein the polymeric material comprises pendant acyl fluoride functionalities or is capable of being derivatized to form pendant acyl fluoride functionalities.

13. The method of claim 1, wherein the solid support is made of a porous or non-porous material.

14. The method of claim 7, wherein the solid support is in a form of threads, sheets, films, gels, membranes, beads, or plates.

15. The method of claim 1, wherein the solid support is fabricated from plastic in the form of a planar device having discrete isolated areas separated by physical barriers to fluid flow, wherein the areas are in the form of wells, troughs, pedestals, hydrophobic or hydrophilic patches, or diecut adhesive reservoirs.

16. The method of claim 15, wherein the solid support is a microplate.

17. The method of claim 15, wherein the plastic is polypropylene and the acyl fluoride functionalities are formed on the discrete isolated areas of the solid support.

18. The method of claim 1, wherein the contacting step is carried out by a technique selected from a group consisting of jet printing, solid or open capillary device contact printing, microfluidic channel printing, silk screening, and a technique using printing devices based upon electrochemical or electromagnetic forces.

19. The method of claim 18, wherein the contacting step is carried out by spotting the unmodified biopolymers to the solid support.

20. The method of claim 1, wherein the condition is a basic pH condition.

21. The method of claim 20, wherein the basic pH condition is maintained in a printing medium at pH of about 8 to 12.

22. The method of claim 21, wherein the printing medium contains a salt.

23. The method of claim 22, wherein the salt is LiCl.

24. The method of claim 21, wherein the printing medium comprises a sodium bicarbonate-carbonate buffer.

25. The method of claim 20, wherein the basic pH condition has a pH of 9–12.

26. The method of claim 1, wherein the biopolymers are polynucleotides, and the polynucleotides are spotted on the solid support under a pH condition of 9–10.

27. The method of claim 1, wherein the biopolymers are polynucleotides, and the polynucleotides are jet printed on the solid support under a pH condition of 10–12.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: synthetic construct

<400> SEQUENCE: 1
cggctggaca cgcttctgta g             21

<210> SEQ ID NO 2
<211> LENGTH: 21
<212> TYPE: DNA
<213> ORGANISM: synthetic construct

<400> SEQUENCE: 2
cggctggaca cgcttctgta g             21

<210> SEQ ID NO 3
<211> LENGTH: 21
<212> TYPE: DNA
<213> ORGANISM: synthetic construct

<400> SEQUENCE: 3
ctacagaagc gtgtccagcc g             21